United States Patent [19]

Wernau

[11] 4,282,321

[45] Aug. 4, 1981

[54] FERMENTATION PROCESS FOR PRODUCTION OF XANTHAN

[75] Inventor: William C. Wernau, Groton, Conn.

[73] Assignee: Pfizer, Inc., New York, N.Y.

[21] Appl. No.: 80,195

[22] Filed: Oct. 9, 1979

Related U.S. Application Data

[63] Continuation-in-part of Ser. No. 964,951, Nov. 30, 1978, abandoned.

[51] Int. Cl.$^3$ .......................... C12P 19/06; C12R 1/64
[52] U.S. Cl. ..................................... 435/104; 435/910
[58] Field of Search ................ 435/101, 104, 813, 910

[56] References Cited

U.S. PATENT DOCUMENTS

| | | | |
|---|---|---|---|
| 3,281,329 | 10/1966 | Lipps | 435/104 |
| 3,391,061 | 7/1968 | McNeely | 435/104 |
| 3,485,719 | 12/1969 | Rogouin | 435/104 |
| 4,119,546 | 10/1978 | Wernau | 252/8.55 D |
| 4,154,654 | 5/1979 | Campagne | 435/104 |

OTHER PUBLICATIONS

Csernus et al., "Xanthan Gum", *Chem. Absts.*, vol. 82, p. 320, (1975), Abs. No. p. 41877c.
Silman et al., "Continuous Fermentation to Produce Xanthan Biopolymer: Effect of Dilution Rate", *Biotech Bioengineering*, vol. XIV, (1972), pp. 23-31.
Charles, *Adv. Biochem. Engin.*, vol. 8, pp. 28-31, 40, 247-248.
Smiley, "Microbial Polysaccharides-A Review", *Food Tech.*, (Sep. 1966) pp. 112-116.
Kouacs et al., "Xanthan Gum" *Food Colloids*, (1977), pp. 500-503.
Rogouin et al., "Production of Polysaccharide with *Xanthomonas Campastris*", *J. Biochem. Microb. Tech. Eng.* vol. III, No. 1 (1961), pp. 51-63.
Moraine et al., "Xanthan Biopolymer Production at Increased Concentration by pH Control", *Biotech. Bioengin.*, vol. XIII, (1971) pp. 381-391.

*Primary Examiner*—Thomas G. Wiseman
*Attorney, Agent, or Firm*—Connolly and Hutz

[57] ABSTRACT

Increased xanthan concentrations are obtained in Xanthomonas fermentations by the gradual addition of a source of assimilable carbon, preferably glucose, to the aqueous nutrient medium during the course of the fermentation cycle.

4 Claims, No Drawings

FERMENTATION PROCESS FOR PRODUCTION OF XANTHAN

CROSS REFERENCE TO RELATED APPLICATIONS

This application is a continuation-in-part of application Ser. No. 964,951 filed Nov. 30, 1978 and now abandoned.

BACKGROUND OF THE INVENTION

There are extensive published reports relating to the production of hydrophilic colloids by the aerobic propagation of bacteria of the genus Xanthomonas in aqueous nutrient media. The earliest work in this field was done at The Northern Regional Research Laboratory of The United States Department of Agriculture at Peoria, Ill. and is described in U.S. Pat. No. 3,000,790. Modified fermentation processes are described in U.S. Pat. Nos. 3,020,206; 3,391,060; 3,427,226; 3,433,708; 3,271,267; 3,251,749; 3,281,329; 3,455,786; 3,565,763; 3,594,280; and 3,391,061.

The hydrophilic colloids produced by Xanthomonas species are polysaccharides which contain mannose, glucose, glucuronic acid, O-acetyl radicals and acetal-linked pyruvic acid. These gums and their derivatives have found wide food and industrial applications. Of special interest is the increasing focus on the use of Xanthomonas polymers in displacement of oil from partially depleted reservoirs.

SUMMARY OF THE INVENTION

The gradual addition of a source of assimilable carbon, preferably glucose, to the aqueous nutrient medium during the course of a Xanthomonas fermentation results in substantially increased xanthan yields.

DETAILED DESCRIPTION OF THE INVENTION

The cost factors involved in secondary and tertiary oil recovery and the competitive use of diluted Xanthomonas whole broths in such recovery dictate the economic imperative of increasing the fermentation concentration of the Xanthomonas polymers. Reduced shipping costs, broth storage facilities and handling costs are some of the benefits derived. Furthermore, reduced volumes of solvent are needed for recovery when initial broth concentrations are high in those processes where Xanthomonas gums are recovered for food, industrial and oil recovery applications.

One of the processes well known to those skilled in the art for increasing the fermentation yield of a desired microbial product is that of adding or "feeding" a nutrient or nutrients during the course of the fermentation cycle. This "feeding" technique may involve the simple intermittent addition of a solution containing a source of assimilable carbon.

Conventional media for the production of xanthan (Xanthomonas polymer) contain a suitable carbohydrate in the aqueous nutrient media at a concentration from about 1 to about 5% w/v. Suitable carbohydrates include, for example, glucose, sucrose, maltose, fructose, lactose, processed inverted beet molasses, invert sugar, high quality filtered thinned starch or mixtures of these carbohydrates. The preferred source of assimilable carbon is glucose.

The use of concentrations of glucose greater than 5% w/v in a typical batch oxidative Xanthomonas fermentation leads to excessive inhibition of Xanthomonas growth and premature cessation of the fermentation. It has been found that this problem can be obviated by the "feeding" of glucose during the course of the Xanthomonas fermentation. The gradual addition of glucose to the fermentation medium initially low or free of glucose not only allows a final glucose addition up to 7% w/v but results in substantially increased xanthan concentration in the final fermentation broth (5% w/v and 70% yield based on total glucose present in the second state inoculum and amount added to the final fermentor). This represents an increase of greater than 60% over a conventional batch process.

The fermentation medium may be selected from any of those described in the literature for the production of xanthan. A preferred chemically defined fermentation medium is described in U.S. Pat. No. 4,119,546.

The addition of glucose solution (approximately 15–50% w/v is started immediately after inoculation. The glucose is fed at an exponentially increasing rate from about 0 to 24 hours after inoculation and at a constant rate from about 24 hours to about 120 hours. Some sugar accumulation (8 grams/liter) occurs during the early stages (peaks at about 48 hours) and drops to nondetectable levels (about 72 hours). Other nutrients may be fed with the source of assimilable carbon without changing the essential nature of the invention.

Air is introduced into the production fermentor via conventional means. Oxygen demand of the fermentation can be matched to equipment limitations of mixing and oxygen transfer in order to reduce toxic acid by-product accumulation. This can be effected by reducing the feed rate of assimilable carbon source until oxygen demand more suitably matches oxygen transfer capacity of the system.

EXAMPLE 1

Cells of Xanthomonas campestris NRRL B-1459 from an agar slant were transferred to 2.8-liter Fernbach flasks each containing 500 ml portions of a medium of the following composition sterilized by autoclaving at 121° C. for 45 minutes:

| Ingredient | Grams/liter |
|---|---|
| Glucose | 10.0 |
| Diammonium phosphate | 2.0 |
| Dihydrogen potassium phosphate | 1.0 |
| Magnesium sulfate | 0.5 |
| Enzymatic digest of casein (NZ Amine YT) | 11.0 |
| pH - 6.8 | |

After shaking for about 22 hours at 28° C., an aliquot sufficient to provide a 5% v/v inoculum was transferred to each of a number of Fernbach flask containing 500 ml of a medium of the following composition sterilized by autoclaving at 121° C. for 45 minutes:

| Ingredient | Grams/liter |
|---|---|
| Glucose (autoclave separately) | 30.0 |
| Ammonium nitrate | 1 |
| Magnesium sulfate | 0.1 |
| Citric acid (anhydrous) | 1.0 |
| Calcium hydroxide | 0.1 |
| Ferrous sulfate | 0.01 |
| Dipotassium hydrogen phosphate | 4.1 |
| Dihydrogen potassium phosphate | 0.69 |
| Manganese sulfate | 0.03 |

| Ingredient | Grams/liter |
|---|---|
| pH - 6.8 | |

After shaking for about 25 hours at 28° C., an amount sufficient to provide a 10% inoculum was transferred to 14 liter Microferm fermentor (New Brunswick Scientific Company, Inc.) with two 4-bladed flat blade turbines (4.7" diameter) and a dissolved oxygen probe.

The fermentor contained 5800 ml of a medium of the following composition sterilized at 121° C. for 45 minutes:

| Ingredient | Grams/liter |
|---|---|
| Ammonium nitrate | 1.0 |
| Magnesium sulfate | 0.01 |
| Citric acid (anhydrous) | 1.0 |
| Disodium hydrogen phosphate | 1.0 |
| Manganese sulfate | 0.03 |
| Ferrous sulfate | 0.01 |
| Calcium hydroxide | 0.01 |
| pH - 6.8 | |

A sterile glucose solution (511 grams in total volume of 1335 ml of water) was fed to the fermentor (incubation temperature of 28° C.) at the following schedule controlled by automatic timer:

| Time (hrs.) | Timer On (sec.) | Timer Off (sec.) | Feed Rate (cc/hr) | Total Accumulated Feed (cc) |
|---|---|---|---|---|
| 0 | 5.0 | 59.3 | 1.49 | 0.00 |
| 1 | 5.2 | 54.8 | 1.66 | 1.49 |
| 2 | 4.9 | 45.8 | 1.86 | 3.15 |
| 3 | 4.9 | 40.7 | 2.06 | 5.01 |
| 4 | 5.0 | 36.9 | 2.29 | 7.07 |
| 5 | 5.0 | 32.9 | 2.53 | 9.36 |
| 6 | 5.0 | 29.0 | 2.82 | 11.9 |
| 7 | 7.0 | 35.9 | 3.13 | 14.7 |
| 8 | 7.0 | 30.5 | 3.58 | 17.8 |
| 9 | 7.0 | 25.7 | 4.11 | 21.4 |
| 10 | 7.0 | 25.0 | 4.65 | 25.5 |
| 11 | 8.0 | 23.4 | 5.33 | 30.2 |
| 12 | 9.0 | 19.3 | 6.11 | 35.5 |
| 13 | 9.0 | 15.8 | 6.97 | 41.6 |
| 14 | 9.0 | 14.2 | 7.93 | 48.6 |
| 15 | 10.0 | 11.2 | 9.06 | 56.5 |
| 16 | 10.0 | 8.9 | 11.0 | 65.6 |
| 17 | 12.0 | 7.4 | 11.9 | 76.6 |
| 18 | 12.0 | 6.8 | 12.3 | 88.5 |
| 19–92 | 12.0 | 6.8 | 12.3 | 100.8–998.7 |
| 92–127 | 12.0 | 12.0 | 9.6 | 998.7–1335 |

During the fermentation, the pH was controlled with 10% NaOH and 10% H$_2$SO$_4$ between 6.5 and 6.9. Dissolved oxygen was controlled by the following fermentor speed schedule:

| Time (hrs.) | Speed (RPM) | Aeration (liters/min.) |
|---|---|---|
| 0 | 400 | 4.0 |
| 19 | 450 | |
| 24 | 470 | |
| 25 | 600 | |
| 26 | 670 | |
| 27 | 720 | |
| 28 | 750 | |
| 30 | 830 | |
| 31 | 860 | |
| 32 | 910 | |
| 33 | 970 | |
| 34 | 1000 | |
| 35 | 900 | |
| 45 | 1000 | |
| 50 | 1012 (max.) | |

The fermentation was conducted for a total period of 136 hours at which time there was no detectable level of glucose. The xanthan concentration was 5.1% w/v with a 70% yield (based on second stage inoculum glucose plus total glucose added to final fermentor). The final viscosity was 42,750 centipoise units as measured at 12 RPM on a Brookfield viscometer.

The process of Example 1 may be repeated replacing glucose in turn with an assimilable source of carbon selected from the group consisting of sucrose, fructose, invert sugar, maltose, lactose, starch, starch hydrolyzates, crude sources of assimilable carbon and mixtures thereof.

I claim:

1. A batch process for producing Xanthomonas biopolymer comprising the steps of aerobically propagating a microorganism of the genus Xanthomonas in an aqueous nutrient medium containing a source of assimilable carbon to form an inocolum, introducing said inocolum into an aqueous medium substantially free of a suitable carbon source, initially feeding at an exponentially increasing rate a source of assimilable carbon into said inocolulated medium under aerobic conditions for 0 to 24 hours, then continuing feeding at a substantially constant rate until a total carbohydrate consumption equivalent to up to about 7% w/v glucose is achieved and recovering the product.

2. The process of claim 1 wherein said source of assimilable carbon is selected from the group consisting of glucose, sucrose, maltose, fructose, lactose, starch, starch hydrolysates, crude sources of said assimilable carbon and mixtures thereof.

3. The process of claim 2 wherein said source of assimilable carbon is glucose.

4. The process of claim 1 wherein the source of assimilable carbon is added to a total of greater than 5% w/v.

* * * * *